United States Patent
Guracar

(10) Patent No.: US 10,675,006 B2
(45) Date of Patent: Jun. 9, 2020

(54) REGISTRATION FOR MULTI-MODALITY MEDICAL IMAGING FUSION WITH NARROW FIELD OF VIEW

(71) Applicant: Siemens Medical Solutions USA, Inc., Malvern, PA (US)

(72) Inventor: Ismayil M. Guracar, Redwood City, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 309 days.

(21) Appl. No.: 14/714,035

(22) Filed: May 15, 2015

(65) Prior Publication Data

US 2016/0331351 A1   Nov. 17, 2016

(51) Int. Cl.
| | | |
|---|---|---|
| *A61B 5/055* | (2006.01) | |
| *A61B 8/08* | (2006.01) | |
| *A61B 8/00* | (2006.01) | |
| *G06T 7/30* | (2017.01) | |
| *A61B 6/03* | (2006.01) | |

(52) U.S. Cl.
CPC ............ *A61B 8/5261* (2013.01); *A61B 5/055* (2013.01); *A61B 8/4254* (2013.01); *A61B 8/4416* (2013.01); *A61B 8/463* (2013.01); *A61B 8/5246* (2013.01); *G06T 7/30* (2017.01); *A61B 6/032* (2013.01); *A61B 8/466* (2013.01); *G06T 2207/10132* (2013.01); *G06T 2207/20221* (2013.01)

(58) Field of Classification Search
None
See application file for complete search history.

(56) References Cited

U.S. PATENT DOCUMENTS

| | | | | |
|---|---|---|---|---|
| 5,891,030 A | * | 4/1999 | Johnson | A61B 6/032 128/920 |
| 5,986,662 A | * | 11/1999 | Argiro | G06T 11/00 345/419 |
| 6,925,200 B2 | * | 8/2005 | Wood | A61B 6/032 382/132 |
| 7,203,266 B2 | * | 4/2007 | Fukuzawa | A61B 6/032 378/4 |
| 7,930,014 B2 | * | 4/2011 | Huennekens | A61B 6/504 382/159 |
| 2002/0035328 A1 | * | 3/2002 | Roundhill | A61B 8/14 600/443 |
| 2002/0077560 A1 | * | 6/2002 | Kramer | A61B 5/0428 600/509 |

(Continued)

FOREIGN PATENT DOCUMENTS

CN   104105449 A   10/2014

OTHER PUBLICATIONS

Brian Porter, "Three Dimensional Medical Ultrasound Acquisition and Data Registration and Fusion"; PhD Thesis, 2014.

(Continued)

*Primary Examiner* — Joanne M Hoffman

(57) ABSTRACT

In multi-modality imaging fusion with ultrasound, one transducer is used for registering ultrasound scan data with scan data from another mode. This registration is used to then align scan data from a different ultrasound transducer with the scan data of the other mode. The alignment may account for differences in position sensing between the two transducers.

19 Claims, 2 Drawing Sheets

(56) References Cited

U.S. PATENT DOCUMENTS

| | | | |
|---|---|---|---|
| 2004/0267111 A1* | 12/2004 | Feinberg | A61B 8/08 600/411 |
| 2007/0003124 A1* | 1/2007 | Wood | A61B 6/032 382/131 |
| 2007/0106146 A1* | 5/2007 | Altmann | A61B 5/042 600/407 |
| 2007/0167787 A1* | 7/2007 | Glossop | A61B 8/00 600/447 |
| 2007/0276226 A1* | 11/2007 | Tal | G06T 7/0026 600/424 |
| 2008/0008369 A1* | 1/2008 | Koptenko | G06K 9/4604 382/128 |
| 2008/0009699 A1* | 1/2008 | Sakas | A61B 8/00 600/407 |
| 2008/0178654 A1* | 7/2008 | Hochmitz | A61B 5/061 73/1.85 |
| 2008/0221446 A1* | 9/2008 | Washburn | A61B 8/00 600/437 |
| 2009/0136109 A1* | 5/2009 | Salgo | A61B 8/0858 382/131 |
| 2010/0063398 A1* | 3/2010 | Halmann | A61B 8/0833 600/459 |
| 2010/0094100 A1* | 4/2010 | Fujii | A61B 8/00 600/300 |
| 2010/0312113 A1* | 12/2010 | Ogasawara | A61B 8/06 600/443 |
| 2011/0028843 A1* | 2/2011 | Hyun | A61B 8/4218 600/443 |
| 2011/0088477 A1* | 4/2011 | Someda | A61B 5/0095 73/641 |
| 2011/0125022 A1* | 5/2011 | Lazebnik | A61B 8/4461 600/444 |
| 2011/0208052 A1* | 8/2011 | Entrekin | A61B 8/0825 600/437 |
| 2011/0270087 A1* | 11/2011 | Yoshida | A61B 8/06 600/443 |
| 2011/0295118 A1* | 12/2011 | Okamura | A61B 8/0825 600/440 |
| 2012/0177265 A1* | 7/2012 | Yoshiara | A61B 5/055 382/128 |
| 2012/0203107 A1* | 8/2012 | Kim | A61B 8/14 600/443 |
| 2012/0209150 A1* | 8/2012 | Zeng | A61N 7/02 601/2 |
| 2012/0253173 A1* | 10/2012 | Endo | G06T 11/008 600/411 |
| 2013/0053679 A1 | 2/2013 | Owen | |
| 2013/0144166 A1 | 6/2013 | Specht et al. | |
| 2013/0172739 A1* | 7/2013 | Paladini | A61B 6/4258 600/436 |
| 2013/0245428 A1* | 9/2013 | Banjanin | A61B 8/4245 600/424 |
| 2013/0245433 A1* | 9/2013 | Deladi | A61B 8/0883 600/424 |
| 2013/0326386 A1* | 12/2013 | Vendrell | G06F 19/321 715/771 |
| 2014/0058266 A1* | 2/2014 | Call | A61B 8/14 600/448 |
| 2015/0178921 A1* | 6/2015 | Hashimoto | A61B 8/13 382/131 |
| 2016/0007970 A1* | 1/2016 | Dufour | A61B 8/4254 600/437 |
| 2016/0345937 A1* | 12/2016 | Deng | A61B 8/4263 |
| 2017/0103540 A1* | 4/2017 | Brokman | G06T 7/20 |

OTHER PUBLICATIONS

W Prager, "Rapid Calibration for 3-D Freehand Ultrasound"; UMB Jul. 24, 1998, (6) 855-69.

\* cited by examiner

REGISTRATION FOR MULTI-MODALITY MEDICAL IMAGING FUSION WITH NARROW FIELD OF VIEW

BACKGROUND

The present embodiments relate to fusion imaging, particularly multi-modality fusion imaging using ultrasound as one of the modes.

Ultrasound imaging may be fused with other modes of imaging, such as computed tomography or magnetic resonance. To fuse or combine information from different modalities, the coordinate systems of the different modalities are registered. The registration allows viewing of the same locations in the patient using the different imaging modes. One approach to registration spatially aligns acquired data from the different modes. However, the field of view for some ultrasound transducers may be narrow. Clear features or other information used for registration may not be available in the narrow field of view. The registration based on scan data may not be reliable or sufficiently accurate where the ultrasound data represents a narrow or small field of view. As a result, fusion imaging is provided but with compromises in fusion image quality due to misalignment.

BRIEF SUMMARY

By way of introduction, the preferred embodiments described below include methods, systems, instructions, and computer readable media for multi-modality imaging fusion. One transducer is used for registering ultrasound scan data with scan data from another mode. This registration is used to then align scan data from a different ultrasound transducer with the scan data of the other mode. The alignment may account for differences in position sensing between the two transducers.

In a first aspect, a method is provided for multi-modality medical imaging fusion. Scan data representing a region of the patient is acquired using a modality other than ultrasound. At least a first part of the region of the patient is scanned with a first ultrasound transducer. The scanning provides first ultrasound data. A sensor detects a first position of the first ultrasound transducer during the scanning with the first ultrasound transducer. The first ultrasound data is spatially registered with the scan data, providing a spatial transform. At least a second part of the region of the patient is scanned with a second ultrasound transducer, providing second ultrasound data. The sensor or another sensor detects a second position of the second ultrasound transducer during the scanning with the second ultrasound transducer. The second ultrasound data is spatially aligned with the scan data as a function of the spatial transform and the first and second positions. A multi-modality fusion image is generated from the scan data and the second ultrasound data, the multi-modality fusion image being a function of the spatially aligning.

In a second aspect, a non-transitory computer readable storage medium has stored therein data representing instructions executable by a programmed processor for multi-modality medical imaging fusion. The storage medium includes instructions for registering multi-modality imaging information acquired with a first ultrasound transducer using a multi-modality coordinate transformation acquired with a second ultrasound transducer, and generating a multi-modality image with the information acquired with the first ultrasound transducer and with the registering of the multi-modality imaging information.

In a third aspect, a system is provided for multi-modality medical imaging fusion. A memory is configured to store magnetic resonance (MR) or computed tomography (CT) data representing a volume of a patient. An ultrasound system is configured to scan the patient with first and second ultrasound transducers, the first ultrasound transducer having a wider field of view than the second ultrasound transducer. A processor is configured to register scan data from the second ultrasound transducer with the MR or CT data using a coordinate transformation matrix for scan data from the first ultrasound transducer with the MR or CT data. A display is configured to display a multi-modality image based on the registration of the scan data from the second ultrasound transducer with the MR or CT data.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Multi-modality fusion is provided with easily translatable coordinate space registration. A wide field-of-view transducer is used to perform cross modality registration. The coordinate transformation matrix from the registration is retained. The coordinate transformation matrix is used after switching to a narrow field-of-view transducer for fused image acquisition. The multimodality coordinate registration transformation acquired with one ultrasound transducer (e.g., wide field-of-view) is used to provide registration information enabling multimodality fusion with a different ultrasound transducer (e.g., narrow field-of-view). The subsequent registration is provided with or without a further registration refinement for the different transducer (e.g., narrow field-of-view).

Figure 1:
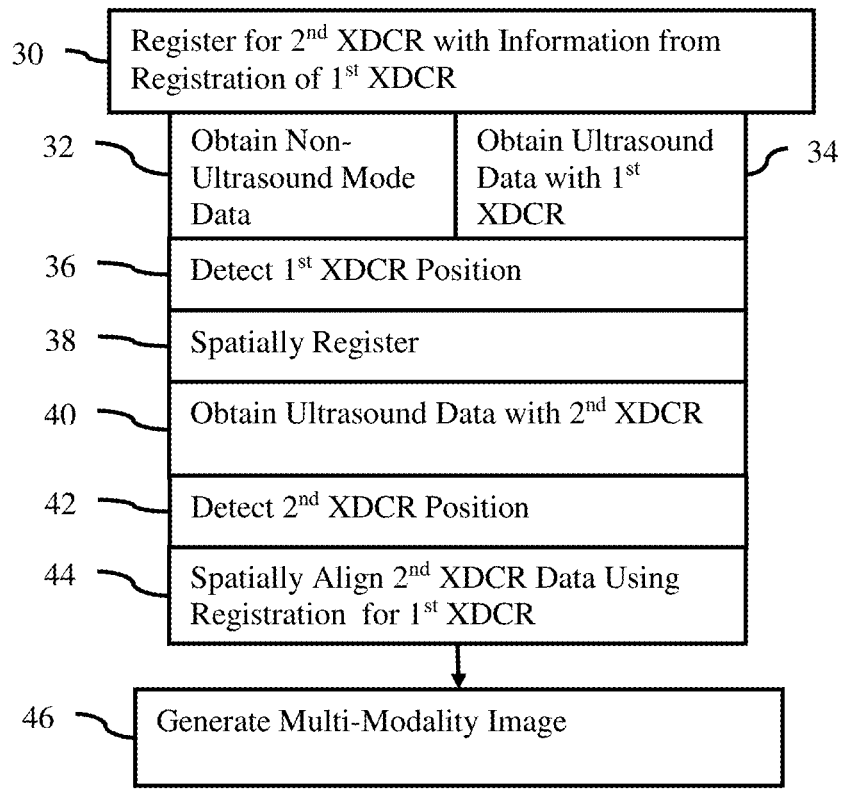
FIG. 1 is a flow chart diagram of one embodiment of a method for multi-modality medical imaging fusion.

FIG. 1 shows a method for multi-modality medical imaging fusion. In general, registration of one transducer with data from another modality is used to align scanning with a different transducer with the data from the other modality. This allows a transducer for scanning with characteristics desired for registration (e.g., wide field of view and/or greater penetration depth) to be used to align scanning for a transducer having characteristics desired for imaging that may not be as optimal for registration (e.g., narrow field of view and/or lesser penetration depth).

Figure 4:
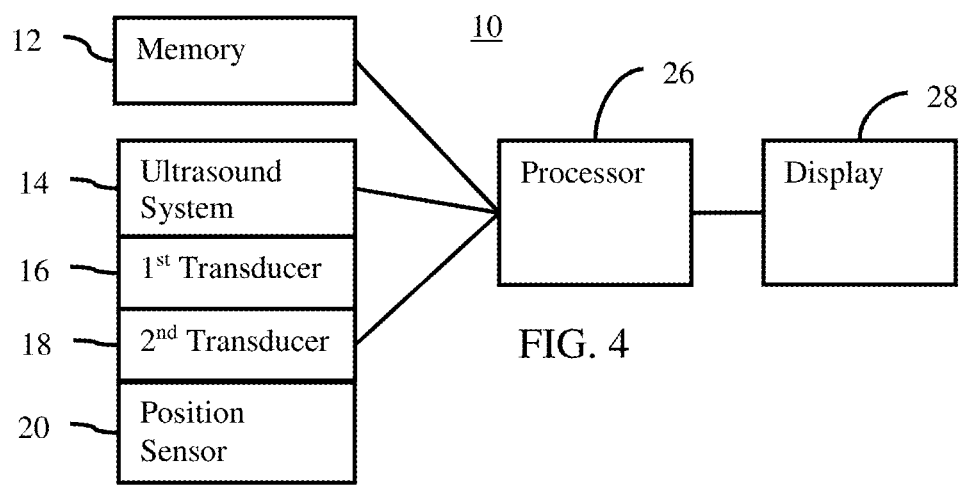
FIG. 4 is a block diagram of one embodiment of a system for multi-modality medical imaging fusion.

The method is implemented by the system 10 of FIG. 4 or another system. Data is obtained using different imaging systems. The ultrasound data is obtained sequentially with different transducers. A sensor and corresponding sensor processor or circuit are used to detect transducer position. A processor or other imaging system performs the registration, alignment, and/or image generation. A display may be used for the imaging. Similarly, a user interface (e.g., input device such as a mouse, trackball, or touch pad and display) allows for input in manual or semi-automated spatial registration or alignment refinement.

The acts are performed in the order shown or other orders. For example, acts 32 and 34 are performed in an interleaved manner, sequentially in either order, or at a same time. Act 36 may be performed prior to, during or after act 34. Similarly, act 42 may be performed prior to, during, or after act 40. As shown, acts 32-38 occur prior to acts 40-44. In other embodiments, act 38 may be performed after act 40 and/or act 42, such as part of act 44.

Additional, different, or fewer acts may be provided. For example, acts 32-44 are one example embodiment for performing act 30. Different acts or sequence may be used for performing act 30. As another example, acts for manual or semi-automatic feature detection and/or user input are provided. In yet another example, act 46 is not provided. The alignment, scan data from different modes, and/or fused image from different modes is stored or transmitted without being displayed as an image.

In act 30, information acquired with one ultrasound transducer is registered with information from a non-ultrasound imaging modality for multi-modality imaging. The registration uses a multi-modality coordinate transformation based on information acquired with a different ultrasound transducer. One transducer is used to register scan data from a probe relative to pre-operative or scan data from a different modality. This pre-registration is then used to align scan data from a different transducer with the pre-operative or scan data from the different modality. Where the different transducers share a common positioning system, the registration from one transducer may be used with the other transducer.

In act 32, scan data is acquired. The scan data is data representing the patient. The scan data is acquired from memory, transfer, or scanning.

The scan data is from a non-ultrasound modality. Any medical imaging modality may be used, such as x-ray, angiography, single photon emission computed tomography, positron emission tomography, magnetic resonance, or computed tomography. For example, a magnetic resonance imaging system acquires magnetic resonance scan data. As another example, a computed tomography system acquires computed tomography data. The scan data is at any stage of processing from raw sensor data to data formatted as an image for display. In magnetic resonance, the raw sensor data is k-space data. After transformation, the received MR data indicates intensities in object space. Different pulse sequences may be used to detect different molecules and/or characteristics at the scan region. In computed tomography, the raw sensor data is projection data. By collecting a series of projections from different angles, tomography may be used to reconstruct density or attenuation as a function of location for a region of the patient.

The scan data of the modality represents a region of a patient. The region is a line, plane, and/or volume of the patient. In one embodiment, the scan data from the non-ultrasound modality represents a torso or other volume region of the patient. For example, the scan data represents voxels in an NxMxO arrangement. Alternatively, the scan data represents a plurality of separate slices (e.g., three parallel slices).

Figure 2:
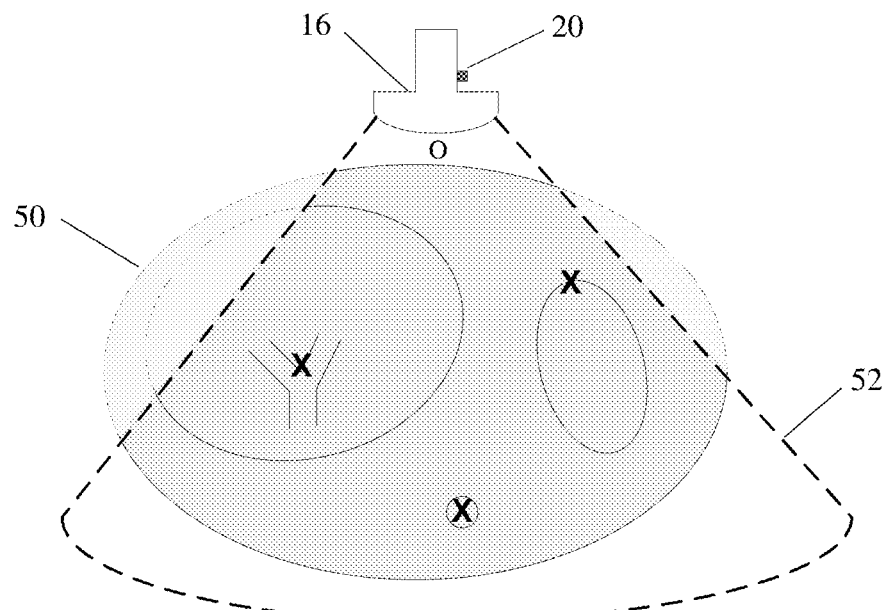
FIG. 2 illustrates an example ultrasound scan relative to a scan region of another imaging modality.

FIG. 2 shows an example where the scan data represents at least a cross-section 50 of a torso of the patient. Various organs and/or features x are included within the region and consequently are represented by the scan data. The scan data may be for an organ and not include an entire cross-section of the patient. In one embodiment, the scan data represents a volume from which a cross-section at any arbitrary orientation may be extracted for imaging a planar region corresponding to a two-dimensional ultrasound scan.

Referring again to FIG. 1, ultrasound data is obtained in act 34. The ultrasound data is acquired from memory, transfer, or scanning. For scanning, an ultrasound imaging system acoustically scans the patient. Any type of scan, scan format, or imaging mode may be used. For example, B-mode, color flow mode, spectral Doppler mode, M-mode, contrast, or other imaging mode is used. The ultrasound imaging system is a different modality than used to acquire the scan data by the other modality.

The ultrasound data represents a point, a line, an area, or a volume of the patient. For example, the ultrasound system performs a two-dimensional B-mode scan of a plane within the patient. The plane is a same plane as represented by the scan data of the other modality. Alternatively, the scanned region in the plane is within a volume of the patient represented by the scan data of the other modality.

The ultrasound data is beamformed data or other data from later in the processing path of an ultrasound system. For ultrasound imaging, waveforms at ultrasound frequencies are transmitted, and echoes are received. The acoustic echoes are converted into electrical signals and beamformed to represent sampled locations within a region of the patient. The beamformed data may be filtered or otherwise processed, such as isolating information a harmonic or fundamental frequency band. Echoes at one or more harmonics of the transmitted waveforms may be processed.

The beamformed data may be detected, such as determining intensity (B-mode) or velocity (flow mode). A sequence of echo signals from a same location may be used to estimate velocity, variance, and/or energy. A sequence may also be used for detecting contrast agents. For example, the response to transmissions with different phases and/or amplitudes is added to isolate information from contrast agents as opposed to tissue or flow. Other detection techniques from the beamformed data may be used. The detected values may be filtered and/or scan converted to a display format. Scan converted data may be mapped to display values of an image.

The scan data from one modality and the ultrasound data from the other modality are acquired with the same spatial resolution. The scan settings for the ultrasound modality and other modality are configured to acquire with the desired sampling resolution. Scan parameter setting, scan conversion, interpolation, extrapolation, decimation, filtering, or other techniques may be used to create data at the desired spatial resolution. In alternative embodiments, the data as acquired in the different modes have different spatial resolution. The data are changed to a common resolution. Interpolation, extrapolation, filtering, decimation, down sampling, up sampling, or other conversion is provided. Alternatively, the scan data from the non-ultrasound modality has a different spatial resolution than the ultrasound data from the ultrasound modality.

The ultrasound data is acquired with a transducer. Any now known or later developed transducer may be used. The transducer, in part, defines a field of view for the scanning. For example, a curved linear transducer may have a greater lateral extent or wider field of view than a linear transducer. With additional steering provided by beamforming, an even greater lateral extent may be provided for the field of view. Different transducers operate over different frequency ranges. Since the depth of the field of view or range extent depends, in part, on frequency, transducers for lower frequency operation may have a greater range extent than transducers for higher frequency operation.

Figure 3:
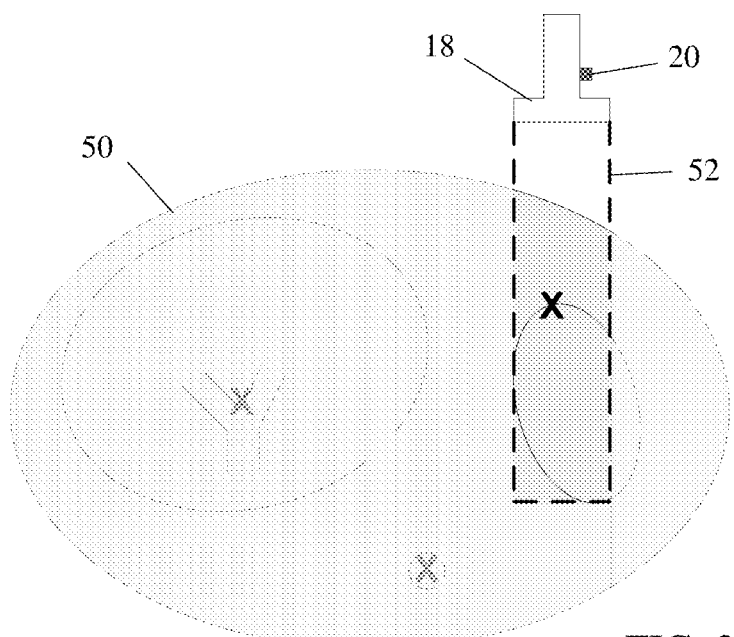
FIG. 3 illustrates another example ultrasound scan relative to a scan region of another imaging modality.

FIGS. 2 and 3 show comparative examples. In FIG. 2, the transducer 16 is a curved linear transducer for low transmit and/or receive frequency (e.g., 1-4 MHz) operation, so has a field of view 52 with a lateral extent and range extent covering most or all of a cross-section 50 of the patient. The field of view 52 overlaps with, is enclosed by, is the same as, or encloses the cross-section 50 from the other modality. Smaller or larger fields of view relative to the region scanned by the other modality may be provided. In FIG. 3, the transducer 18 is a linear transducer for high transmit and/or receive frequency (e.g., 4-10 MHz) operation, so has a field of view 52 less than ½, ⅓, or other factor of area or volume of the field of view 52 of the other transducer 16. For example, the field of view 52 of the transducer 16 is 10 cm wide at a widest, but more or less coverage may be provided. The field of view of the transducer 18 is less than 2 cm wide at a widest, but more or less coverage may be provided. Similarly, the field of view 52 is less by a same or different factor than the cross-section 50 of the scan data from the other modality.

For fusion imaging, the ultrasound imaging is to be spatially registered with the scan data from the other modality. Where the scan data and ultrasound data are used for registration, data representing a larger region of the patient may result in more accurate registration. Accordingly, the user selects or is instructed to select scanning with a wider field of view and/or lower frequency transducer for registration than used for the desired ultrasound imaging in the fusion image. For example, the curved linear array of FIG. 2 is selected so that the ultrasound data represents a larger region with additional or more clearly provided features, fiducials, anatomy, or other markers used for registration. In the embodiment represented in FIGS. 2 and 3, the field of view 52 of the transducer 18 includes one feature x while the field of view 52 of the transducer 16 includes three features x. For acquiring ultrasound data for registration, the transducer 16 with the larger field of view 52 is used.

Referring again to FIG. 1, a position of the transducer during the acquisition of the ultrasound data with the transducer is detected in act 36. When the transducer with the desired characteristics for registration (e.g., wide and/or deep field of view) is scanning, the position, and/or orientation of the transducer is measured. The measurement is during the scanning, just prior to the scanning, and/or just after the scanning. The position and/or orientation may be measured multiple times during the scanning for one image or frame of data. One measure is selected or a combination of measures (e.g., average) is used. For on-going or subsequent scans of the same region for subsequent images or frames of ultrasound data, separate measures are made and used.

Any position sensing may be used. The sensor includes a component spaced from the transducer. In one embodiment, a magnetic position sensor is provided. Three coils or other antennas are connected to or are in the transducer. A separate device generates a magnetic field. The position and orientation of the transducer is detected from signals from the three coils or antennas in response to the magnetic field. Alternatively, an antenna in or on the transducer generates the magnetic field and antennas located elsewhere determine the position of the transducer. In other embodiments, an optical sensor or camera detects the position and/or orientation of the transducer. Ultrasound or other sensors for triangulating the position of the transducer may be used.

The sensor is fixed to or within the transducer. The transducer includes a housing. The sensor is within or on the housing and cannot be removed without opening the transducer probe and/or using tools. A different sensor is positioned for each transducer, but may be used with a common base unit or remotely positioned antenna. In an alternative embodiment, the sensor is usable on different transducers. The sensor clips or otherwise releasably attaches to or in the transducer. The sensor may be removed from one transducer and placed on another transducer.

The position sensor is used to determine the position of the different transducers so that the ultrasound data from the different transducers is positioned in a same frame of reference. The sample density provided by beamformer relates ultrasound data from one transducer relative to another assuming a same scan plane and origin. The position sensor provides the information for positioning to a same scan plane and origin and/or positioning relative to each other. Alternatively or additionally, since the position of the transducer in the coordinate space for the imaging modality used to acquire the non-ultrasound scan data is not known, the position sensor may be used for a coarse positioning of the transducer relative to the patient. The relative position of the field of view 52 to the region of the patient represented by the scan data is then refined with further registration.

In act 38, the ultrasound data is registered with the non-ultrasound data. The data from both modalities represents a part of the patient. The scan data may represent more of the patient, but the ultrasound data represents a portion also represented by the scan data. Where the transducer position sensor and the imaging system for the non-ultrasound modality are not registered, the portion represented by data of both modes is not known. The relative translation, rotation, and/or scale are not known. Since different systems are used to acquire the ultrasound and scan data, different coordinates, samples, pixels, or voxels may represent different locations in the patient. The spatial registration determines the portion of the patient represented by both the ultrasound data and the scan data. The spatial registration finds the location of the field of view relative to the patient representation of the scan data. The data and corresponding coordinate systems of the data are aligned so that the data of both types of data representing a given location of the patient are known. The spatial relationship of the coordinate systems is determined.

The ultrasound and scan data from the different modalities are used to spatially register. Using rigid or non-rigid transforms, the translation, rotation, and/or scaling of the ultrasound data to the scan data or vice versa is determined. The registration is based on the entire frames of data. Alternatively, a sub-set of the data, such as a region of interest is used. Multiple regions for the same frames may be used. In one example, the scan data is converted to emulate ultrasound data. The synthesized ultrasound data is registered with the acquired ultrasound data.

Any technique may be used for registration. Speckle or feature-based registration may be used. The features are anatomical, but may instead be fiducials or inserted instruments. By locating landmark features as points, lines, areas, and/or volumes in both sets of data, the spatial registration between the different types of data is determined. The spatial transform to align the features in the two data spaces is calculated. The scale, rotation, and/or translation to align or spatially register the different data are found from the features. In another approach, one set of data is translated, rotated, and/or scaled relative to the other by different amounts. The registration uses correlation, minimum sum of absolute differences, or other measure of similarity to find the translation, rotation, and/or scale associated with the best match.

In yet another registration technique, trained filters, such as machine-learnt classifiers, generate probability response maps. Different data is selected for filtering or classifying to identify a spatial registration with similar probability response maps. Identification of specific landmarks may be avoided.

The registration is automatic or manual. The features are found by user input or automatically by a processor. A processor finds the spatial registration for automatic. Features are located automatically, such as with a machine-trained classifier. The processor then calculates the spatial transform from the identified features. For manual registration, the user views images generated from both modalities and alters the plane used for imaging from the scan data to find an image corresponding to the ultrasound image, or vice versa. Semi-automatic approaches may be used, such as the user inputting the same features for images from both modalities, and the processor determining the registration from the user input features. As another semi-automatic approach, the user inputs a bounding box or region of interest in images from both modalities to guide feature detection.

The spatial registration provides a multi-modality coordinate transformation of an ultrasound scan with the ultrasound transducer with scan data (e.g., magnetic resonance or computed tomography data). A coordinate transformation matrix capturing the translation, orientation, and/or scale of the ultrasound data relative to the scan data of the other modality is determined. The matrix is determined in response to user specified landmarks or features (x) or automated or semi-automated guidance to align ultrasound and other modality images or data.

In the example of FIGS. 2 and 3, the landmark features x are anatomical point, line, area, or volume features. While only one volume or area feature may be used, multiple features of any dimensionality may improve the registration. By locating the same features, x, from both the ultrasound data and the scan data from the other modality, the translation, rotation, and/or scale of the ultrasound data with the transducer at a particular position is found relative to the scan data from the other modality. The wide field of view 52 allows landmarks to be more likely represented in the ultrasound data and more easily located and co-registered between ultrasound and scan data of the other modality. The width and/or depth of the field of view 52 being greater may more likely provide for accurate registration.

The spatial transformation matrix is stored or retained. Where other scans with the same or different transducer use the same position sensing, the retained matrix may be used to register the other scans without repeating the data-based registration. The data-based registration may be repeated, but with increased processing speed using an initial registration determined by the spatial registration of act 38.

In act 40, a different transducer with a same or different ultrasound imaging system is used to scan the patient. The patient is scanned with ultrasound as discussed above for act 34, but using a different transducer. A new frame or set of ultrasound data representing the patient at a given time is acquired. The part of the patient represented is in the same or different plane than the scan of act 34. The scan of act 40 may have a shallower and/or narrower field of view than for act 34. The area and/or volume scanned are smaller. For example, the width of the field of view is less by a factor of two or more. Alternatively or additionally, the depth of the field of view is less by a factor of 1.5 or more. Lesser factors may be used. Because of the smaller field of view, the acquired ultrasound data may represent less of the patient. Alternatively, the field of view is larger or the same.

The user may desire the spatial resolution or other imaging characteristic provided by a given transducer. However, that transducer may have a sufficiently small field of view or other characteristic to result in a less accurate spatial registration. The user first scans with a transducer to acquire data for spatial registration, then switches to the desired imaging transducer with the smaller field of view for multi-modality or fusion imaging with another modality.

In the example of FIGS. 2 and 3, the subsequent scan is shown in FIG. 3. For example, a higher frequency linear transducer is used as compared to the curved linear lower frequency transducer of FIG. 2. In FIG. 3, the field of view is smaller in width and has a more limited penetration depth, making it difficult to locate the landmarks to achieve co-registration of ultrasound with scan data of another modality. The limited field of view makes it very difficult for sonographers and/or a processor to find co-located landmarks in the live ultrasound set and stored scan data set of the other modality. The high frequency of the linear array, however, provides better resolution.

In act 42, the sensor detects the position of the transducer during, before, or after the scanning. The detection discussed above is performed, but for the other transducer (i.e., the transducer selected for generating multi-modality images). For example, a magnetic position sensor is used to detect the position and orientation of the transducer during scanning to acquire a frame of ultrasound data representing part of the patent at a given time.

In one embodiment, the sensor connected with the transducer is releasable, such as being clipped or otherwise latched to the transducer. The sensor from the transducer used for creating the spatial transformation matrix is removed and added to the transducer used for imaging. Once clipped on, the sensor is used to detect the position and orientation of the transducer during scanning. A base unit or remote antenna is used with the sensor to detect. In other embodiments, the same base unit or remote antenna is used, but a different sensor is attached to the imaging transducer. Using the same base unit or remote antenna allows position and orientation detection of both transducers, even with different sensors, in a same coordinate system or frame of reference.

In act 44, the ultrasound data acquired for imaging from the scan of act 40 is spatially aligned with the scan data from the other modality. Rather than repeating or in addition to repeating the spatial registration of act 38, the spatial alignment is performed with the retained spatial transform. The spatial transform indicates a translation, rotation, and/or scale to equate the position of the transducer and corresponding field of view relative to the scan data from the other modality. The coordinate transform from the first transducer with the scan data is used for the data from the second transducer.

The spatial transform is adjusted to account for the difference in positions of the different transducers. The imaging transducer may not be in the same position as the transducer used for registration. The spatial alignment of the field of view relative to the scan data accounts for this change or difference in position. The spatial transform may be altered to account for the difference. Alternatively, a further spatial transform in translation and/or rotation is applied to account for the difference in position and orientation of the different transducers.

The location of the sensor on the different transducers may be at a different location relative to the array of elements. To account for this difference, an origin is assigned to the ultrasound data or scans. Any origin may be used, such as a center of the array at the face of the array or another lateral and/or depth location. The same or different origin is used for each of the scans. The difference in distance and orientation of the different transducers depends on the position of the sensor located within the probe as well as the preferred coordinate space origin for the transducer scan format. The spatial transform is adjusted (e.g., altered or an addition transform applied) to account for the difference. The coordinate transformation matrix is adjusted to account for differences in the position of the position sensor with respect to the origin in the ultrasound data set between the different transducers.

By applying the spatial transform, the location of the field of view relative to the region of the patient represented by the scan data of the other modality is determined. The coordinate systems of the scan data and ultrasound data are aligned. The scan data representing the same locations in the field of view of the ultrasound scan or at least scan data representing the same plane or field of view are identified using the spatial transform.

In another embodiment, further spatial registration is performed. The alignment from the spatial transform is an initial or coarse alignment. Further alignment occurs. Features are identified or other spatial registration is performed to adjust the alignment. The ultrasound data for the scan used for imaging is spatially registered to refine the alignment. Alternatively, the user manually adjusts the alignment.

In act 46, a multi-modality image is generated. Any now known or later developed multi-modality imaging may be used. The information from two different modalities, one of which is ultrasound, is fused for a combined presentation to the user. The ultrasound data from the scan of act 40 and the scan data obtained in act 32 are both used for imaging.

The information from both modalities represents a same region of the patient. The spatial alignment is used to select the scan data to be used for imaging. In this way, the part of the image from the non-ultrasound modality represents the same plane, volume, or other patient region. The scan data may be selected to represent more, the same, or less than the part represented by the ultrasound image. The selected scan data is used to generate or render at least part of the multi-modality image. All or a selected portion of the ultrasound data is used to generate or render at least part of the multi-modality image. For example, a cross-section or planar image for a same plane as scanned for ultrasound is generated from the scan data, and an ultrasound image is also generated for the field of view in that plane.

In alternative embodiments, the scan data selected for imaging relies on the spatial transform for selection, but is of a different part of the patient than represented by the ultrasound data. For example, the ultrasound image is of a particular plane in an organ, and the scan data is selected for imaging an adjacent organ or organs. The spatial transformation matrix aligns the coordinate systems for selection of the scan data for imaging.

Any type of fusion may be provided in the fusion image. In one embodiment, the ultrasound information is overlaid on the information from the other modality. The ultrasound information is colored or mapped differently to differentiate from the information from the other modality. For example, the information from the other modality is mapped to grayscale, and the ultrasound information is mapped to color. Where information from both modalities is provided for a given location, then the information is combined (e.g., averaged) or information from one modality is selected (e.g., select ultrasound). Thresholding or other selection criteria may be used.

In another type of fusion, the fusion image is formed from separate images of the different modalities displayed adjacent to each other at a same time. The images do not overlap on the screen, but are displayed together. For example, an ultrasound image is displayed next to a computed tomography or magnetic resonance image of the same portion of the patient.

The generated fusion image is a one, two, or three-dimensional image. For two-dimensional imaging, the scan data and/or ultrasound data are interpolated to a display format for the plane. Alternatively, the scan data and/or ultrasound data are formatted along the plane as acquired. For three-dimensional imaging, projection, surface, or other rendering is performed from a viewing direction. The same or different viewing direction is used for the scan data as for the ultrasound data. The information from the different modalities is combined into the same one, two, or three-dimensional image.

In alternative embodiments, different image generation is used for the different modalities. For example, the ultrasound data is scan converted and displayed as a two-dimensional image of a field of view in a plane of the patient. The fused image also includes information from the other modality, such as a three-dimensional rendering of a region of the patient that includes or is intersected by the plane. The plane may be used as a clipping surface for the rendering.

The image is a static image representing the patient at a given time. In other embodiments, the ultrasound part of the image is updated in real-time or as a sequence. As new ultrasound scans occur due to repetition of act 40, the ultrasound portion of the fused image is updated with the most recently acquired ultrasound data. During the sequence of scans, the transducer may be moved relative to the patient. The alignment from the position sensor may be updated as the position of the transducer changes.

Other imaging may be provided. For example, one or more images generated from the scanning of act 34 are generated. These images may be generated to assist in obtaining a frame of data representing the desired features for registration. Alternatively or additionally, images from the scan of act 34 are added to the fusion image to provide further information. The fusion image includes information acquired with both transducers.

FIG. 4 shows a system 10 for multi-modality medical imaging fusion. The system 10 includes a memory 12, an ultrasound system 14, transducers 16 and 18, a sensor 20, a processor 26, and a display 28. Additional, different, or fewer components may be provided. For example, a network or network connection is provided, such as for networking with a medical imaging network or data archival system. As another example, a user interface is provided. In yet another embodiment, a system for scanning with a different modality (e.g., magnetic resonance or computed tomography system) is provided instead of or in addition to the memory 12. The ultrasound system 14 may not be provided in some embodiments, such as where the ultrasound data is acquired by transfer or from storage.

The processor 26 and display 28 are part of a medical imaging system, such as the ultrasound system 14, other modality system, or other system. Alternatively, the processor 26 and display 28 are part of an archival and/or image processing system, such as associated with a medical records database workstation or server. In other embodiments, the processor 26 and display 28 are a personal computer, such as desktop or laptop, a workstation, a server, a network, or combinations thereof.

The display 28 is a monitor, LCD, projector, plasma display, CRT, printer, or other now known or later developed devise for outputting visual information. The display 28 receives images, graphics, or other information from the processor 26, memory 12, or ultrasound system 14. A display buffer outputting to the display 28 configures the display 28 to display an image.

One or more images representing a region of the patient are displayed. At least some of the values of the image are determined, at least in part, from a non-ultrasound modality and at least some of the values of the image are determined, at least in part, from the ultrasound system 14. For example, both ultrasound and magnetic resonance or computed tomography values are included in the fused image. Any fused or multi-modality image may be presented on the display 28. The registration scan is used by the processor 26 to generate the multi-modality image output by the display 28.

The memory 12 is a graphics processing memory, video random access memory, random access memory, system memory, cache memory, hard drive, optical media, magnetic media, flash drive, buffer, database, combinations thereof, or other now known or later developed memory device for storing data or video information. The memory 12 is part of an imaging system (e.g., ultrasound system 14), part of a computer associated with the processor 26, part of a database, part of another system, or a standalone device.

The memory 12 stores datasets (e.g., frames) each representing a three-dimensional patient volume or a two-dimensional patient area. The patient volume or area is a region of the patient, such as a region within the chest, abdomen, leg, head, arm, or combinations thereof. The patient area or volume is a region scanned by the ultrasound system 14 and represented by scan data from another modality (e.g., scanned by a magnetic resonance or computed tomography system).

Any type of data may be stored, such as medical image data (e.g., ultrasound and magnetic resonance or computed tomography anatomy data). The data represents the patient at one time or includes frames representing the patient over time, such as prior to or during treatment or other procedure.

The stored data is interpolated or converted to an evenly spaced two or three-dimensional grid or is in a scan format. The data for different modalities may be transformed to be on a same grid or format. The data from different modalities may be spatially registered or may be data prior to spatial registration.

Alternatively or additionally, the memory 12 or other memory is a non-transitory computer readable storage medium storing data representing instructions executable by the programmed processor 26 for multi-modality imaging. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The ultrasound system 14 is any now known or later developed ultrasound imaging system. For example, the ultrasound system 14 includes two or more transducers 16, 18 for converting between acoustic and electrical energies. The transducers 16, 18 connect to different ports on the ultrasound system 14 or releasably connect to the same port at different times.

The transducers 16, 18 are one-, two-, or multi-dimensional arrays of piezoelectric or capacitive membrane elements. In one embodiment, the transducer 16 is a curved linear or phased array, and the other transducer 18 is a linear array. Other combinations of transducer types may be used. The different transducers 16, 18 have different fields of view, such as one having a wider and the other narrow field of view. Alternatively, both transducers 16, 18 have a same or similar lateral extent of the field of view. The different transducers 16, 18 operate at different frequency bands, such as completely distinct bands or overlapping bands but with different higher or lower limits. As a result of the frequency band of operation, the different transducers have different depth extent for the field of view. Alternatively, the transducers 16, 18 have a same or similar frequency range of operation and corresponding depth of penetration.

The transducers 16, 18 are used to scan the patient with ultrasound. Transmit and receive beamformers relatively delay and apodize signals for different elements of the transducers 16, 18. Acoustic energy is used to scan a plane and/or volume. For example, a volume is scanned by sequentially scanning a plurality of adjacent planes. Any format or scan technique may be used. The scanned volume may intersect or include all of the patient volume. B-mode, Doppler, or other detection is performed on the beamformed signals. A scan converter, memory, three-dimensional imaging processor, and/or other components may be provided. The ultrasound data is output in a polar coordinate or scan converted Cartesian coordinate format.

The ultrasound system 14 is configured by software, hardware, or both to acquire one or more frames of ultrasound data representing the patient. Different ultrasound data is acquired by the different transducers 16, 18. For example, one transducer 16 is used for imaging as well as spatial registration. Another transducer 18 uses the spatial registration from the one transducer 16 to image in a fused or multi-modality format.

The position sensor 20 is a magnetic position sensor, camera, ultrasound triangulation system, gyroscope, or other position and/or orientation sensor. In one embodiment, the sensor 20 includes an antenna or target on the transducer 16, 18 and another antenna or target remote from the transducer 16, 18. The remote portion provides a common frame of reference for detecting the position and/or orientation of the sensor 20 on the transducer 16, 18.

A separate sensor 20 is provided on each transducer 16, 18, but with use of the common remote portion. In an alternative embodiment, the sensor 20 is external to and releasably connects with the transducer 16, 18. A clip-on or other temporally attachable sensor 20 allows the same sensor 20 to be used on the different transducers 16, 18 at different times. When one of the transducers 16, 18 is used for scanning, the sensor 20 is connected to or in the transducer 16, 18. When the other transducer 18, 16 is used for scanning, the sensor 20 is connected to or in that transducer 18, 16.

The processor 26 is a general processor, central processing unit, control processor, graphics processor, digital signal processor, three-dimensional rendering processor, image processor, application specific integrated circuit, field programmable gate array, digital circuit, analog circuit, combinations thereof, or other now known or later developed device for spatially registering, determining a spatial transform, spatially aligning, and/or generating a fusion image. The processor 26 is a single device or multiple devices operating in serial, parallel, or separately. The processor 26 may be a main processor of a computer, such as a laptop or desktop computer, or may be a processor for handling tasks in a larger system, such as the ultrasound system 14.

The processor 26 is configured by software and/or hardware. The processor 26 is configured to register scan data from one ultrasound transducer with scan data from another modality, such as magnetic resonance or computed tomography data. For fusion imaging, the processor registers the different types of data to generate an image representing the same part of the patient with different modalities. Since the field of view of some transducers is limited, using ultrasound data from such transducers to register may not be as accurate as using ultrasound data from transducers with larger fields of view. The processor 26 is configured to register using a coordinate transformation matrix created using a transducer with a larger field of view. The matrix is determined by spatially registering the ultrasound scan data from the ultrasound transducer 16 with the larger field of view with the scan data from the other modality. Manual, automatic, or semi-automatic spatial registration is performed to determine the translation, rotation, and/or scale for the coordinate transformation matrix. This matrix is then applied to ultrasound data from the other transducer 18.

The positions (e.g., location and orientation) of the transducers 16, 18 during the scanning are used to further register. The processor 26 determines the difference in position as well as difference in scan format for the different transducers 16, 18 and accounts for this difference in the registration. Once the ultrasound scan data of the transducer 18 is registered using the matrix from registration using the ultrasound scan data of the other transducer 16, the processor 26 generates the fusion or multi-modality image.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for multi-modality medical imaging fusion, the method comprising:
    acquiring scan data representing a region of the patient, the scan data being of a modality other than ultrasound, the modality other than ultrasound comprising x-ray, angiography, single photo emission computed tomography, positron emission tomography, magnetic resonance, or computed tomography;
    scanning at least a first part of the region of the patient with a first ultrasound transducer comprising a first probe, the scanning providing first ultrasound data;
    detecting, with a sensor, a first position of the first ultrasound transducer during the scanning with the first ultrasound transducer;
    spatially registering the first ultrasound data with the scan data, the spatially registering providing a spatial transform relating a first coordinate system of the first probe with a scan data coordinate system of the scan data;
    scanning at least a second part of the region of the patient with a second ultrasound transducer comprising a second probe, the scanning providing second ultrasound data;
    detecting, with the sensor or another sensor, a second position of the second ultrasound transducer during the scanning with the second ultrasound transducer;
    spatially aligning the second ultrasound data from the second ultrasound transducer with the scan data of the modality other than ultrasound, the spatially aligning relating a second coordinate system of the second probe to the scan data coordinate system, the spatially aligning being an adjustment of the spatial transform from a difference between the first and second positions of the first and second ultrasound transducers and application of the adjusted spatial transform between the scan data and the second ultrasound data so that locations in the patient represented in the second scan data are known in the scan data; and
    generating a multi-modality fusion image from the scan data and the second ultrasound data, the multi-modality fusion image being a function of the spatially aligning, the multi-modality fusion image comprising the scan data as x-ray, angiography, single photo emission computed tomography, positron emission tomography, magnetic resonance, or computed tomography data fused with the second ultrasound data.

2. The method of claim 1 wherein acquiring comprises acquiring the scan data as the magnetic resonance or computed tomography data.

3. The method of claim 1 wherein scanning with the first ultrasound transducer comprises scanning with a first field of view, and wherein scanning with the second ultrasound transducer comprises scanning with a second field of view with an area or volume less than the first field of view by a factor of at least two.

4. The method of claim 1 wherein scanning with the first ultrasound transducer comprises scanning at a first transmit frequency, and wherein scanning with the second ultrasound transducer comprises scanning at a second transmit frequency greater than the first transmit frequency by a factor of at least 1.5.

5. The method of claim 1 wherein detecting the first and second positions comprises detecting with the sensor comprising a magnetic position sensor.

6. The method of claim 5 wherein detecting the first and second positions comprises detecting with the sensor releasably clipped to the first ultrasound transducer and then detecting with the sensor releasably clipped to the second ultrasound transducer.

7. The method of claim 1 wherein spatially registering comprises generating the spatial transform as a function of landmark features represented in both the scan data and the first ultrasound data.

8. The method of claim 1 wherein spatially aligning comprises spatially aligning as a function of the spatial transform, the first and second positions, and first and second origins of the first and second ultrasound data, respectively.

9. The method of claim 1 wherein scanning with the second ultrasound transducer, detecting the second position, and spatially aligning are performed after the scanning with the first ultrasound transducer, detecting the first position, and spatially registering.

10. The method of claim 1 wherein generating the multi-modality fusion image comprises generating with information from the second ultrasound data as an overlay on information from the scan data.

11. In a non-transitory computer readable storage medium having stored therein data representing instructions executable by a programmed processor for multi-modality medical imaging fusion, the storage medium comprising instructions for:
registering multi-modality imaging information acquired with a first ultrasound transducer probe using multi-modality coordinate transformation acquired with a second ultrasound transducer probe, the multi-modality coordinate transformation relating spatial locations of the patient between the second ultrasound transducer probe and another modality; and
generating a multi-modality image with the information acquired with the first ultrasound transducer probe and with the registering of the multi-modality imaging information, the multi-modality image comprising a combination (a) ultrasound and (b) x-ray, angiography, single photo emission computed tomography, positron emission tomography, magnetic resonance, or computed tomography, the ultrasound represented by the information acquired with the first ultrasound transducer probe.

12. The non-transitory computer readable storage medium of claim 11 wherein registering comprises determining the multi-modality coordinate transformation of an ultrasound scan with the second ultrasound transducer probe with magnetic resonance or computed tomography data.

13. The non-transitory computer readable storage medium of claim 11 wherein registering comprises adjusting the multi-modality coordinate transformation as a function of a difference in sensor position and scan origin between the first and second ultrasound transducer probes.

14. The non-transitory computer readable storage medium of claim 11 wherein registering comprises determining the multi-modality coordinate transformation with the second transducer probe having a greater field of view than the first ultrasound transducer probe.

15. The non-transitory computer readable storage medium of claim 11 wherein generating comprises generating the multi-modality image as an ultrasound image from the first ultrasound transducer probe of a region of a patient and an image of another modality formatted to represent the region.

16. A system for multi-modality medical imaging fusion, the system comprising:
a memory configured to store magnetic resonance (MR) or computed tomography (CT) data representing a volume of a patient;
an ultrasound system configured to scan the patient with first and second ultrasound transducers, the first ultrasound transducer being a first array having a wider field of view than a second array of the second ultrasound transducer;
a processor configured to register scan data from the second ultrasound transducer with the MR or CT data using a coordinate transformation matrix for scan data from the first ultrasound transducer with the MR or CT data, the coordinate transformation matrix relating locations in the patient for the scan data from the first ultrasound transducer with the MR or CT data, the registration relating locations in the patient for the scan data from the second ultrasound transducer with the MR or CT data; and
a display configured to display a multi-modality image based on the registration of the scan data from the second ultrasound transducer with the MR or CT data, the multi-modality image comprising a combination of the MR or CT data and the scan data from the second ultrasound transducer.

17. The system of claim 16 further comprising:
a position sensor connected with the first ultrasound transducer, the second ultrasound transducer, or both;
wherein the registration, the coordinate transformation matrix, or both is a function of position from the position sensor.

18. The system of claim 16 wherein the scan data from the second ultrasound transducer is acquired with a higher frequency than the scan data from the first ultrasound transducer.

19. The method of claim 1 wherein scanning with the first ultrasound transducer comprises B-mode scanning, and wherein scanning with the second ultrasound transducer comprises B-mode scanning.

* * * * *